US012521531B2

(12) United States Patent
Wong et al.

(10) Patent No.: US 12,521,531 B2
(45) Date of Patent: Jan. 13, 2026

(54) INTERVENTIONAL MEDICAL DEVICE WITH BALLOON-ACTUATED COVER

(71) Applicant: Medtronic, Inc., Minneapolis, MN (US)

(72) Inventors: Thomas A. Wong, Little Canada, MN (US); Jonathan E. Baxter, Fridley, MN (US); Kevin R. Seifert, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 662 days.

(21) Appl. No.: 17/964,766

(22) Filed: Oct. 12, 2022

(65) Prior Publication Data

US 2024/0123197 A1 Apr. 18, 2024

(51) Int. Cl.
*A61M 25/10* (2013.01)
*A61N 1/05* (2006.01)
*A61M 25/00* (2006.01)

(52) U.S. Cl.
CPC ............. *A61M 25/10* (2013.01); *A61N 1/057* (2013.01); *A61M 2025/0079* (2013.01); *A61M 2025/0089* (2013.01); *A61M 2025/105* (2013.01)

(58) Field of Classification Search
CPC ............ A61B 17/3211; A61B 17/3494; A61B 17/3496; A61B 2017/32113; A61M 25/0068; A61M 25/0069; A61M 25/0074; A61M 25/0082; A61M 25/0084; A61M 25/0618; A61M 25/10; A61M 25/1006; A61M 25/1009; A61M 2025/0024; A61M 2025/0042; A61M 2025/0057; A61M 2025/0089; A61M 2025/0091; A61M 2025/1043; A61M 2025/1068; A61M 2025/1093
See application file for complete search history.

(56) References Cited

U.S. PATENT DOCUMENTS 5,211,652 A * 5/1993 Derbyshire ........ A61B 17/3213 606/206
5,820,595 A 10/1998 Parodi
(Continued)

FOREIGN PATENT DOCUMENTS

WO 2017/165810 9/2017

OTHER PUBLICATIONS

International Search Report and Written Opinion for PCT/IB2023/059450 dated Nov. 3, 2023 (10 pages).

*Primary Examiner* — Kami A Bosworth
(74) *Attorney, Agent, or Firm* — Mueting Raasch Group

(57) ABSTRACT

Medical devices including a balloon-actuated sheath are provided. The medical devices include a tubular body, a tooltip, a balloon, and a tubular sheath translatably coupled to the balloon. Medical devices including a balloon-actuated distal cap are provided. The medical devices include a tubular body, a tooltip, a balloon, and a distal cap translatably coupled to the balloon. When air is pushed into one end of the medical device, the balloon may inflate, translating the tubular sheath or distal cap along a longitudinal axis from a retracted position to an extended position. When in the extended position, the tubular sheath at least partially surrounds the tooltip. When in the extended position, the distal cap at least partially opens fluid communication between the tooltip and the environment.

15 Claims, 5 Drawing Sheets

(56) References Cited

U.S. PATENT DOCUMENTS

| | | | |
|---|---|---|---|
| 7,879,004 | B2 | 2/2011 | Seibel et al. |
| 10,512,757 | B2 | 12/2019 | Laby et al. |
| 10,575,950 | B2 | 3/2020 | Mclean |
| 10,675,164 | B2 | 6/2020 | Green et al. |
| 2002/0045929 | A1 | 4/2002 | Diaz |
| 2004/0002726 | A1 | 1/2004 | Nunez et al. |
| 2004/0267308 | A1 | 12/2004 | Bagaoisan et al. |
| 2008/0091073 | A1 | 4/2008 | Park |
| 2010/0168665 | A1 | 7/2010 | Skerven |
| 2011/0144743 | A1 | 6/2011 | Lattouf |
| 2011/0270126 | A1 | 11/2011 | Gunday et al. |
| 2013/0304181 | A1 | 11/2013 | Green et al. |
| 2015/0057738 | A1 | 2/2015 | Hepke et al. |
| 2015/0209558 | A1 | 7/2015 | Charlebois et al. |
| 2018/0200483 | A1 | 7/2018 | Laby et al. |
| 2018/0325712 | A1 | 11/2018 | Bialas et al. |
| 2020/0069917 | A1 | 3/2020 | Laby et al. |

* cited by examiner

INTERVENTIONAL MEDICAL DEVICE WITH BALLOON-ACTUATED COVER

FIELD

The present disclosure is related to medical devices including balloons and interventional medical devices including balloons. Specifically, this disclosure relates to tubular interventional medical devices including a cover actuated by an elastic balloon for use in the body.

SUMMARY

A medical device includes a tubular body defining a longitudinal axis, the tubular body comprising: a distal end; an inner lumen extending along the longitudinal axis; and an outer surface. A tooltip is attached to the tubular body at the distal end of the tubular body. A balloon extends circumferentially around the tubular body, the balloon including: a proximal portion fixedly coupled to the tubular body; a distal portion; and a radially inflatable middle portion between the proximal portion and the distal portion of the balloon, the inflatable middle portion comprising an inner volume in fluid communication with the inner lumen of the tubular body. A tubular sheath including a distal opening is translatably coupled to the balloon at the distal portion of the balloon, the tubular sheath being translatable along the longitudinal axis between a retracted position and an extended position. In the extended position, the tubular sheath at least partially surrounds the tooltip.

The balloon has an inflated configuration, wherein when the balloon is in the inflated configuration, the tubular sheath is in the extended position. The balloon has a deflated configuration, wherein when the balloon is in the deflated configuration, the tubular sheath is in the retracted position.

The tooltip may include a fixation mechanism, such as an active fixation mechanism. The tooltip may include a helix, a blade, a lead, or an electrode. The tooltip may include a hypodermic needle fluidly couplable to the at least one inner lumen of the tubular body. The tooltip may include an anti-inflammatory steroid or an anticoagulant.

The balloon may include an elastomer. The balloon may be a silicone balloon. The balloon may be a latex balloon. The distal portion of the balloon may be fixedly coupled to the tubular body.

The tubular sheath may be substantially conical. The tubular sheath may be substantially cylindrical. The tubular sheath may include plastic, glass, or metal. The tubular sheath may include silicon, latex, polyurethane, polytetrafluoroethylene, or polyetheretherketone. The tubular sheath may include platinum, iridium, titanium, stainless steel, or nitinol.

The tubular body may include plastic, glass, or metal. The tubular body may include a thermoplastic. The tubular body may include polyurethane, CARBOTHANE™ PELLETHANE®, ELASTHANE™, polyether block amide, ARNITEL®, or silicone. The tubular body may include braided metal. The tubular body may include a metal coil.

A medical device includes a tubular body defining a longitudinal axis, the tubular body including a distal end; an inner lumen extending along the longitudinal axis; and an outer surface. A tooltip is attached to the tubular body at the distal end of the tubular body. A balloon extends circumferentially around the tubular body, the balloon including: a proximal portion fixedly coupled to the tubular body; a distal portion; and a radially inflatable middle portion between the proximal portion and the distal portion of the balloon, the inflatable middle portion comprising an inner volume in fluid communication with the inner lumen of the tubular body. A distal cap including one or more openings is translatably coupled to the balloon at the distal portion of the balloon, the distal cap being translatable along the longitudinal axis between a retracted position and an extended position, wherein in the extended position, the distal cap at least partially opens fluid communication between the tooltip and an environment.

The tooltip may include a tooltip lumen extending along the longitudinal axis, wherein in the extended position, the distal cap at least partially opens fluid communication between the tooltip lumen and an environment. The tooltip may include an electrode, wherein in the extended position, the distal cap opens fluid communication between the electrode and an environment, and a plurality of electrodes, wherein the distal cap has a first extended position that opens fluid communication between a first electrode and the environment and a second extended position that opens fluid communication between a second electrode and the environment.

A method of using the medical device may include inserting a distal end of a tubular body of the medical device through an introduction site of a patient; at least partially inflating a balloon extending circumferentially around and fixedly attached to the tubular body to extend a tubular sheath translatably attached to the balloon, wherein the tubular sheath is extended to at least partially surround a tooltip located at the distal end of the tubular body; advancing the medical device through the patient from the introduction site to a target site; at least partially deflating the balloon; and using the tooltip at the target site.

A method of using the medical device may include inserting the distal end of the tubular body of the medical device through an introduction site of a patient; at least partially inflating the balloon; advancing the medical device through the patient from the introduction site to a target site; and using the tooltip at the target site. In some embodiments, the balloon is at least partially inflated prior to advancing the medical device through the patient from the introduction site to a target site and wherein the balloon is deflated after advancing and prior to using the tooltip at the target site. In some embodiments, the balloon is at least partially inflated after advancing the medical device through the patient from the introduction site to a target site and prior to using the tooltip at the target site.

Figure 1A:
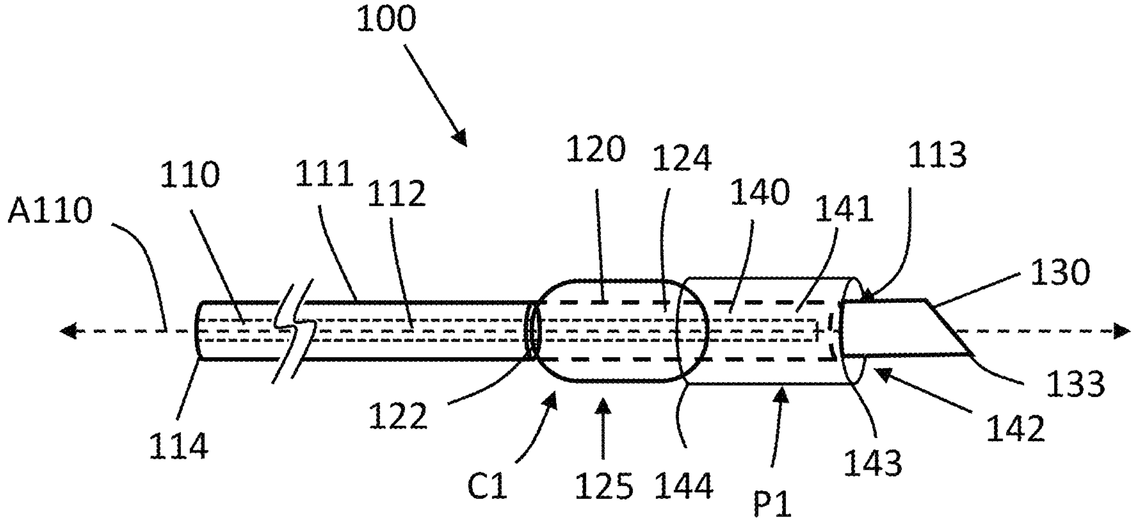
FIG. 1A is a perspective view of a medical device in accordance with one or more embodiments of the present disclosure with a tubular sheath in a retracted position.

The figures are rendered primarily for clarity and, as a result, are not necessarily drawn to scale. Moreover, various structure/components may be shown diagrammatically or removed from some or all of the views to better illustrate aspects of the depicted embodiments, or where inclusion of such structure/components is not necessary to an understanding of the various exemplary embodiments described herein. The lack of illustration/description of such structures/components in a particular figure is, however, not to be interpreted as limiting the scope of the various embodiments in any way.

DEFINITIONS

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, the terms "polymer", "polymerized monomers", and "polymeric material" include, but are not limited to, organic homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and atactic symmetries.

The term "substantially" as used here has the same meaning as "significantly," and can be understood to modify the term that follows by at least about 90%, at least about 95%, or at least about 98%.

The term "not substantially" as used here has the same meaning as "not significantly," and can be understood to have the inverse meaning of "substantially," i.e., modifying the term that follows by not more than 25%, not more than 10%, not more than 5%, or not more than 2%.

In this disclosure, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively unless the context specifically refers to a disjunctive use.

The recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to", "at most", or "at least" a particular value, that value is included within the range.

As used here, "have," "having," "include," "including," "comprise," "comprising," or the like are used in their open-ended sense, and generally mean "including, but not limited to." It will be understood that "consisting essentially of," "consisting of," and the like are subsumed in "comprising" and the like. As used herein, "consisting essentially of," as it relates to a composition, product, method, or the like, means that the components of the composition, product, method, or the like are limited to the enumerated components and any other components that do not materially affect the basic and novel characteristic(s) of the composition, product, method, or the like.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Reference in the specification to "some embodiments," "an embodiment," "one embodiment," "embodiments" or "other embodiments" means that a particular feature, structure, or characteristic described in connection with the embodiments is included in at least some embodiments, but not necessarily all embodiments, of the present disclosures.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

The terms "proximal" and "distal" are used herein to indicate directions from the viewpoint of a user, such as a medical professional using the medical device described herein. The proximal end is the end closest to the user, and the distal end is the end farthest away from the user. The distal end in this context typically refers to a free end of the device.

In several places throughout the application, guidance is provided through examples, which examples, including the particular aspects thereof, can be used in various combinations and be the subject of claims. In each instance, the recited list serves only as a representative group and should not be interpreted as an exclusive list. It is to be understood that the particular examples, materials, amounts, and procedures are to be interpreted broadly in accordance with the scope and spirit of the invention as set forth herein.

For any method disclosed herein that includes discrete steps, the steps may be conducted in any feasible order. And, as appropriate, any combination of two or more steps may be conducted simultaneously.

All headings throughout are for the convenience of the reader and should not be used to limit the meaning of the text that follows the heading, unless so specified.

DETAILED DESCRIPTION

Conventional interventional medical devices are used in interventional procedures to diagnose and treat patients, often avoiding the need for more invasive surgical procedures. In an interventional procedure, an interventional medical device is directed through a patient's body to a target site tissue for therapy and/or diagnosis. The device is often either torque-controlled or flow-directed to the target site. In many examples of interventional medical devices that are flow-directed, a balloon is used to guide the device from the introduction site to the target site.

Interventional medical devices typically include tools, usually located at the tip of the device, that interact with or administer treatment to the target site of the patient. Such tools may be delicate and therefore prone to being damaged during delivery from the introduction site to the target site. It would be desirable to provide a protection mechanism that can protect the tool against damage. It would further be desirable to provide a protection mechanism that can guard against contact with the tool during delivery before the tool has reached its intended target site. It would be desirable to provide a protection mechanism that can be removed to expose the tool when contact with the patient's tissue is desired.

An example of an interventional medical device is a temporary pacing lead which may be used to provide pacing therapies to non-ambulatory or semi-ambulatory patients. Flow-directed temporary pacing leads utilize a balloon to guide the lead from the introduction site, through the venotomy, and into the appropriate location within the heart. A flow-directed pacing lead often uses passive fixation methods, which are prone to dislodgement. Dislodgement interrupts the delivery of pacing therapy to the patient and typically requires the pacing lead to be repositioned by a training physician or clinical specialist. Patients that are more ambulatory present a greater dislodgement risk. As described herein, a pacing lead with an active fixation method, such as a screw-in helix, can be used to decrease risk of dislodgement. Furthermore, a patient using a temporary pacing lead with an active fixation method may enjoy increased ability to ambulate in the hospital.

It may be desirable for an active fixation mechanism, such as a screw-in helix, to be protected from contact with the patient's non-target tissue to protect the helix from damage and also to protect the patient's tissue prior to intended fixation of the helix in the patient's heart. To improve safety and efficacy of therapy with an active fixation lead, it may be desirable to protect the helix during delivery, and to selectively expose the helix when it is time to fixate the lead into the heart at the desired location.

As illustrated with this example, safety and efficacy of interventional medical devices can be improved by protecting the tool at the tip of an interventional medical device from being damaged while being directed to the target site within a patient's body and by protecting the patient's non-target tissue from interactions with the tool. As described herein, an interventional medical device utilizing a balloon-actuated cover provides a mechanism to mask and protect the device's tool during delivery, and to expose the tool when necessary for the procedure. The motion created by the inflation of a balloon at the tip of the interventional medical device is used to create linear actuation, which moves a cover to at least partially surround or uncover the tool. The cover may be a sheath or cap that can partially or completely cover the tool and that can be moved to partially or completely uncover the tool. In some embodiments, when the balloon is deflated, the sheath retracts proximally to expose the tool (e.g., a helix) and allow the tool to be used (e.g., allow the lead to be fixated using the helix). In other embodiments, when the balloon is inflated, the cap is pushed forward to open fluid communication between the tool (e.g., an electrode or an open lumen) and the environment and allow the tool to be used.

According to an embodiment, a balloon positioned along a medical device, such as a lead or catheter of an interventional medical device, is used to actuate a sheath. The balloon may be a dual-purpose balloon. That is, the balloon may serve a typical function, such as to guide a flow-directed device from the introduction site to the target site, as well as serve as the actuator for the sheath. The sheath may be used to mask or protect a tool during delivery of the lead. For example, the sheath may be used to mask or protect a tool that is sharp, such as a screw-in helix of an active fixation temporary pacing balloon lead, or a blade. The sheath may be moved to expose the tool when use of the tool is desired. The tool may be positioned at the distal tip of the medical device (e.g., a lead or catheter). The sheath and balloon may be immediately adjacent the tool. According to an embodiment, inflation of the balloon at the distal tip creates linear actuation, which moves the sheath forward and over the tool. When the balloon is deflated, the sheath retracts proximally, exposing the tool.

According to an embodiment, the balloon-actuated sheath is used with a medical device including a tubular body with a lumen. The medical device may be an interventional medical device. That is, the medical device may include parts that are inserted into a patient's body. Exemplary embodiments of such medical devices include leads and catheters. However, the balloon-actuated sheath can be used with other medical devices, as well. The balloon-actuated sheath of the present disclosure is not particularly limited by the primary use of the medical device. On the other hand, the balloon-actuated sheath may be particularly useful with devices that already include a balloon that serves a primary purpose.

Referring now to FIG. 1A, an exemplary medical device 100 is shown. According to an embodiment, the medical device 100 has a tubular body 110 defining a longitudinal axis A110, a proximal end 114 and a distal end 113. The tubular body 110 has an outer surface 111 and at least one inner lumen 112. According to an embodiment, the inner lumen 112 extends parallel to or along the longitudinal axis A110. The inner lumen 112 may extend along part of the length of the tubular body 110 or along the entire length of the tubular body 110. The medical device 100 may optionally have a plurality of lumens. The plurality of lumens may be coextensive and extend parallel to one another, or the medical device 100 may include one or more lumens that are not parallel to the inner lumen 112. According to an embodiment, a tooltip 130 is attached to the tubular body 110 at the distal end 113 of the tubular body 110. Any suitable or desirable tooltip may be used. In the embodiment shown, the tooltip 130 is a blade.

The medical device 100 includes a balloon 120. The balloon 120 extends circumferentially around the tubular body 110. The balloon 120 has a proximal portion 122 that is fixedly coupled to the tubular body 110. The balloon 120 has an opposing distal portion 124 and a radially inflatable middle portion 125 between the proximal and distal portions 122, 124 of the balloon 120. The inflatable middle portion 125 has an inner volume V125. The inner volume V125 is in fluid communication with the inner lumen 112 of the tubular body 110 (e.g., via one or more passageways, holes, perforations, pores, or slits (not shown) in the tubular body 110). Therefore, gas or liquid (e.g., air) pushed through the inner lumen 112 can be used to inflate the balloon 120.

Figure 1B:
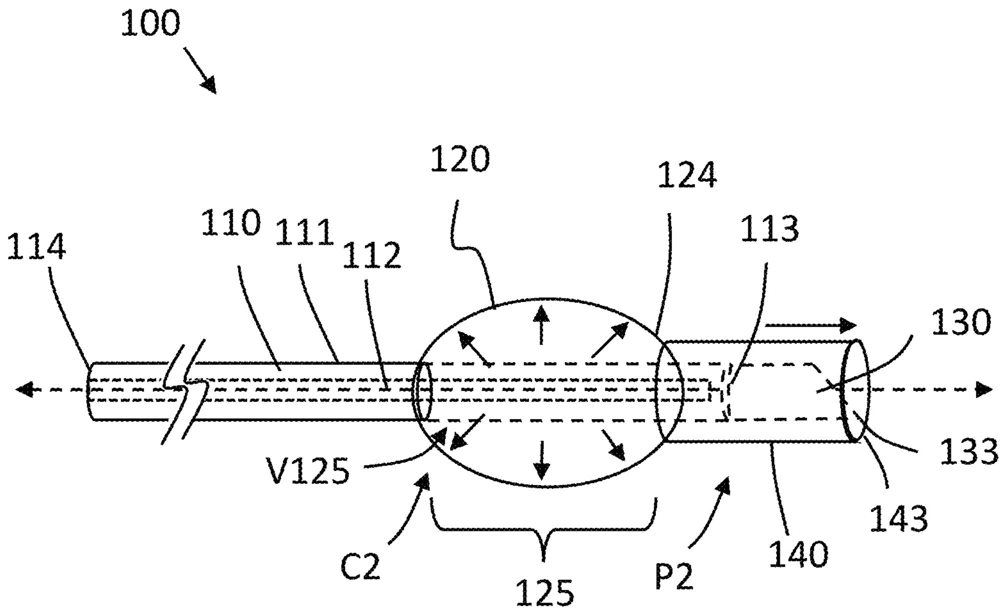
FIG. 1B is a perspective view of the medical device of FIG. 1A with the tubular sheath in an extended position.

A tubular sheath 140 is translatably coupled to the balloon 120 at the distal portion 124 of the balloon 120. The tubular sheath 140 has hollow body 141 with a distal opening 142 at the distal end 143 of the tubular sheath 140. According to an embodiment, the tubular sheath 140 is axially translatable. The tubular sheath 140 is translatable along the longitudinal axis A110 between a retracted position P1 (FIG. 1A) and an extended position P2 (FIG. 1). In the retracted position P1, the tooltip 130 is at least partially exposed. In the extended position P2, the tubular sheath 140 at least partially surrounds (e.g., covers, shields, or protects) the tooltip 130. As the balloon 120 is inflated (that is, as it transitions from a deflated configuration to an inflated configuration), the balloon expands in at least one of the distal portion (at least distally), the middle portion (at least radially), and the proximal portion (at least proximally). As the balloon 120 expands distally, the tubular sheath 140 is translated distally because it is translatably coupled to the distal portion of the balloon 120. Likewise, as the balloon 120 is deflated (that is, as it transitions from an inflated to a deflated configuration), it contracts in at least one of the distal portion (at least proximally), the middle portion (at least radially), and the proximal portion (at least distally). As the balloon 120 contracts proximally, the tubular sheath 140 is translated proximally because it is translatably coupled to the distal portion of the balloon 120.

The balloon 120 has a deflated configuration C1 and an inflated configuration C2. According to an embodiment, when the balloon 120 is in the deflated configuration C1, the tubular sheath 140 is in the retracted position P1. When the balloon 120 is in the inflated configuration C2, the tubular sheath 140 is in the extended position P2. The balloon 120 may be partially inflated and the tubular sheath 140 may be correspondingly partially extended.

The balloon-actuated sheath of the present disclosure is not particularly limited by the construction and configuration of the medical device. In some embodiments, the tubular body 110 of the medical device 100 is made of plastic, glass, metal, or a combination thereof. For example, the tubular body 110 may be made of a thermoplastic. In some embodiments, the tubular body 110 includes one or more of polyurethane, CARBOTHANE™, PELLETHANE®, ELASTHANE™, polyether block amide, ARNITEL®, or silicone. The tubular body 110 may include braided metal. The tubular body 110 may include a metal coil. The tubular body 110 may have any suitable outer diameter. For example, the tubular body 110 may have an outer diameter of between 0.5 mm and 4 mm. For example, the outer diameter of the tubular body 110 may be 0.5 mm or greater, 0.75 mm or greater, 1 mm or greater, 1.5 mm or greater, or 2 mm or greater. The outer diameter of the tubular body 110 may be 4 mm or less, 3 mm or less, or 2 mm or less. The tubular body 110 may have any suitable axial length. For example, the tubular body 110 may have an axial length of 35 cm or greater, 50 cm or greater, or 75 cm or greater. The tubular body 110 may have an axial length of 110 cm or less, 90 cm or less, or 80 cm or less. The tubular body 110 may have an axial length of 35 cm to 110 cm.

The balloon-actuated sheath of the present disclosure is not particularly limited by the construction and configuration of the tooltip. That is, the balloon-actuated sheath may be used with many different types of tooltips, as long as the balloon-actuated sheath is sized to fit over the tooltip (or at least a part of the tooltip) and can be actuated to uncover the tooltip. In one embodiment, the tooltip 130 is or includes a fixation mechanism, such as an active fixation mechanism. An active fixation mechanism is a mechanism that can be used to fixate the medical device 100 to a tissue of the patient. An example of an active fixation mechanism is a helical tip, shaped like a small cork screw. The tooltip 130 may be or may include a helix, a blade, a lead, an electrode, or a combination thereof. The tooltip 130 may be or may include a hypodermic needle. The hypodermic needle may be fluidly couplable to the inner lumen 112 or a secondary lumen extending through the tubular body 110. In some embodiments, the tooltip 130 includes a distal cap. In some embodiments, the tooltip 130 may include or be doped with an active agent, such as an anti-inflammatory steroid, an anticoagulant, or another drug for release over time when in contact with the patient's blood. The tooltip 130 may optionally include moving parts. The tooltip 130 may be movable relative to the tubular body 110 or may be immovable and fixedly attached to the tubular body 110. The tooltip 130 may be releasably attached to the distal end 113 of the tubular body 110. The tooltip 130 may be interchangeable. The tubular body 110 may also include one or more additional tooltips. The one or more additional tooltips may have the same or a different construction and function as the primary tooltip 130.

The balloon 120 may be attached to the tubular body 110 by any suitable attachment mechanism. For example, the balloon 120 may be adhered to the tubular body 110 by an adhesive, self adhesion, friction fit, interference fit, thermal bond, or by using a coupling device, such as an O-ring. In some embodiments, the outer surface 111 of the tubular body 110 includes a circumferential channel or groove. The proximal portion 122 of the balloon 120 may be fixedly coupled to the tubular body 110 at the circumferential channel. In some embodiments, the balloon 120 is made of a material that adheres to the tubular body 110 without additional adhesives or fixation mechanisms.

The balloon may have any suitable construction and composition in view of its use in an interventional medical device. The balloon may be made from any suitable expandable material. For example, the balloon may be made of an elastomer. Suitable elastomers include, for example, silicone, natural rubber latex, synthetic rubber latex, neoprene, nitrile, and the like, and combinations thereof. In some embodiments, the balloon is made of or includes silicon. In some embodiments, the balloon is made of or includes latex. The balloon 120 may have any suitable shape and size. In the deflated configuration C1, the balloon 120 may have an internal diameter of between 0.5 mm and 4 mm. For example, the internal diameter of the balloon in the deflated configuration C1 may be 0.5 mm or greater, 0.75 mm or greater, 1 mm or greater, 1.5 mm or greater, or 2 mm or greater. The internal diameter of the balloon in the deflated configuration C1 may be 4 mm or less, 3 mm or less, or 2 mm or less. In the deflated configuration C1, the balloon 120 may have a wall thickness between 0.1 mm and 1 mm. For example, the wall thickness of the balloon in the deflated configuration C1 may be 0.1 mm or greater, 0.125 mm or greater, 0.15 mm or greater, 0.2 mm or greater, or 0.3 mm or greater. The wall thickness of the balloon in the deflated configuration C1 may be 1 mm or less, 0.75 mm or less, 0.5 mm or less, 0.4 mm or less, or 0.3 mm or less. The inflatable middle portion 125 of the balloon 120 may have an axial length in the deflated configuration C1 of 1 mm or greater, 2 mm or greater, 3 mm or greater, mm or greater, or 5 mm or greater. The inflatable middle portion 125 of the balloon 120 may have an axial length of 60 mm or less, 50 mm or less, 40 mm or less, 30 mm or less, 25 mm or less, 20 mm or less, 15 mm or less, or 10 mm or less. The dimensions of the balloon 120 in the inflated configuration C2 depend on the dimensions of the balloon in the deflated configuration C1 and the extent of the inflation. In some embodiments, the balloon 120 is capable of moving the sheath 140 by 1 mm or greater. While there may not be a desired upper limit, in practice, the balloon 120 may be capable of moving the sheath 140 by 5 mm or less.

The tubular body 110 may have a proximal end 114 in fluid communication with an attachment coupling. The proximal end 114 of the tubular body 110 may be connected to a proximal controller or proximal connector. The proximal controller may be used to control, guide, and operate the tubular body 110, the balloon 120, the tubular sheath 140, and the tooltip 130. The balloon 120 may be inflated by injecting a fluid (e.g., air or other gas or liquid) through the tubular body 110.

The balloon 120 may be attached to the tubular body 110 at one or both ends of the balloon 120. The proximal portion 122 of the balloon 120 is attached to the tubular body 110 between the proximal end 114 and the distal end 113 of the tubular body 110 of the medical device 1. In some embodiments, only the proximal portion 122 of the balloon 120 is fixedly attached to the tubular body 110. In some embodiments, both the proximal portion 122 and the distal portion 124 of the balloon 120 are fixedly coupled to the tubular body 110.

The tubular sheath 140 may have any suitable size, shape, and construction. In some embodiments, the tubular sheath 140 is cylindrical or substantially cylindrical, as shown. Alternatively, the outer diameter of the tubular sheath 140 may vary along its length. For example, the tubular sheath 140 may be conical or substantially conical. The tubular sheath 140 may have a circular cross section. The tubular sheath 140 may have a non-circular cross section. The distal end 143 of the tubular sheath 140 may have an outer diameter that is greater than the proximal end 144 of the tubular sheath 140. The tubular sheath 140 may be made from any suitable materials. For example, the tubular sheath 140 may include or be made of plastic, glass, metal, or a combination thereof. In some embodiments, the tubular sheath 140 is made of a polymer, such as silicon, latex, polyurethane, polytetrafluoroethylene, polyetheretherketone, or a combination thereof. In some embodiments, the tubular sheath 140 includes or is made of platinum, iridium, titanium, stainless steel, nitinol, or a combination thereof.

Figure 2A:
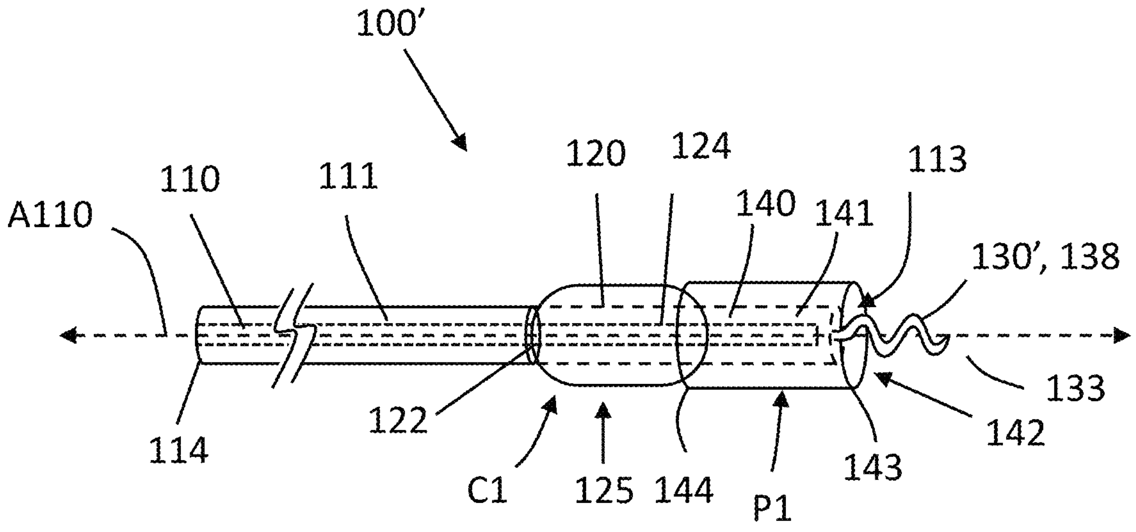
FIG. 2A is a perspective view of a medical device in accordance with one or more embodiments of the present disclosure with a tubular sheath in a retracted position.
Figure 2B:
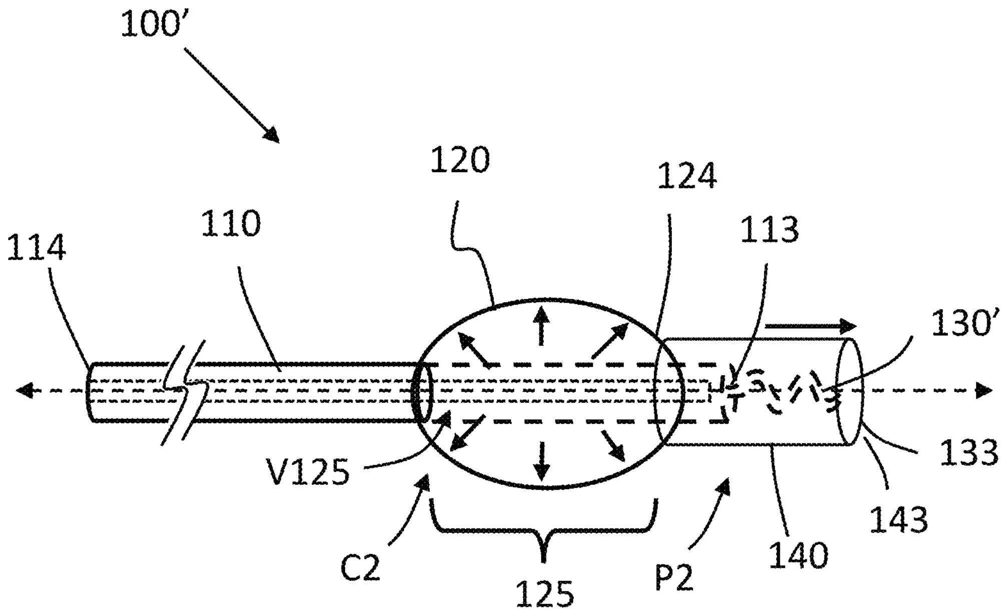
FIG. 2B is a perspective view of the medical device of FIG. 2A with the tubular sheath in an extended position.

An alternative embodiment of the medical device 100' is shown in FIGS. 2A and 2B. The medical device 100' is otherwise similar to the device shown in FIGS. 1A and 1B except that the tooltip 130' includes a helical active fixation mechanism 138'. The balloon 120' may be used to axially translate the tubular sheath 140' to cover and uncover the tooltip 130'.

Figure 3A:
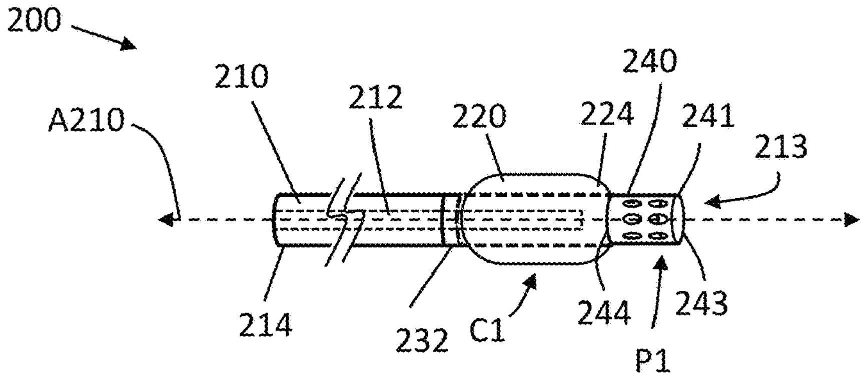
FIG. 3A is a perspective view of a medical device in accordance with one or more embodiments of the present disclosure with a distal cap in a retracted position.
Figure 3B:
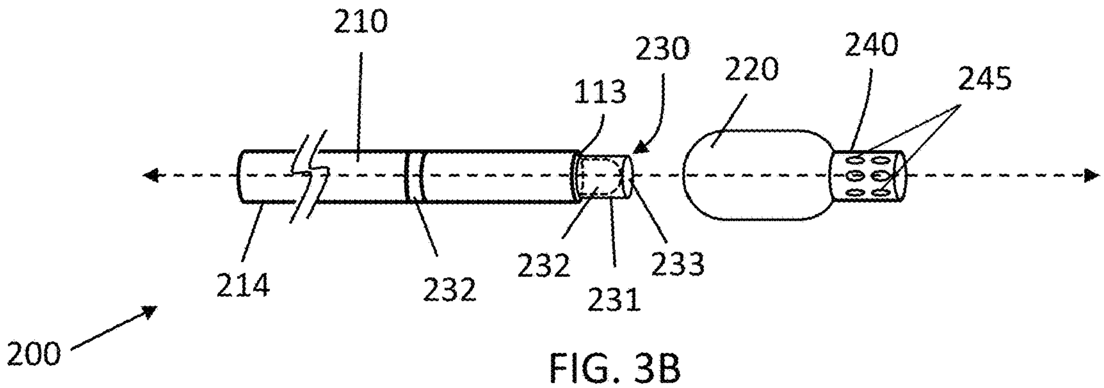
FIG. 3B is a partially exploded perspective view of the medical device of FIG. 3A.
Figure 3C:
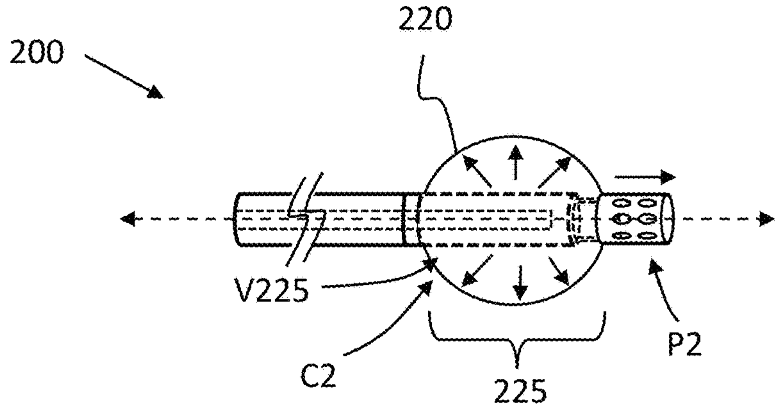
FIG. 3C is a perspective view of the medical device of FIG. 3A with the distal cap in an extended position.

Referring now to FIGS. 3A-3C, an exemplary medical device 200 is shown. According to some embodiments, the medical device 200 may include a balloon-actuated distal cap 240 alternatively or additionally to the balloon-actuated sheath. In such embodiments, the distal cap 240 may be actuated to selectively open and close fluid communication between the environment (e.g., a patient's bloodstream) and one or more components of the medical device 200. In such embodiments (as shown in FIG. 3A) the medical device 200 includes a tubular body 210 defining a longitudinal axis A210. The tubular body 210 has at least one inner lumen 212. In one or more embodiments, the inner lumen 212 extends parallel to or along the longitudinal axis A210. The inner lumen 212 may extend along part of the length of the tubular body 210 or along the entire length of the tubular body 210.

According to an embodiment, medical device 200 includes a tooltip 230 (shown in FIG. 3B) attached to the tubular body 210 at the distal end 213 of the tubular body 210. The tooltip 230 may include a tooltip lumen 231. The tooltip lumen 231 may extend parallel to or along the longitudinal axis A210 (e.g., proximally from the distal end 213 of the tubular body 210 toward a proximal end 214 of the tubular body 210). The tooltip lumen 231 may have at least one opening (such as the opening 233 shown in FIG. 3B).

The distal cap 240 is translatably coupled to a balloon 220 at a distal portion 224 of the balloon 220. The distal cap 240 has a hollow body 241 with one or more openings 245 in the hollow body 241. The one or more openings 245 may be distributed radially about the hollow body 241. The distal cap 240 is translatable along the longitudinal axis A210 between a retracted position P1 (FIG. 3A) and an extended position P2 (FIG. 3C). The distal cap 240 telescopically receives the tooltip 230.

The balloon 220 has a deflated configuration C1 and an inflated configuration C2. In some embodiments, when the balloon 220 is in the deflated configuration C1, the distal cap is in the retracted position P1. When the balloon 220 is in the inflated position C2, the distal cap 240 is in the extended position P2. The balloon 220 may be partially inflated and the distal cap 240 may be correspondingly partially extended.

In the retracted position P1, the distal cap 240 at least partially receives the tooltip 230 and closes fluid communication between the tooltip lumen 231 and an environment. In some embodiments, in the retracted position P1, the one or more openings 245 of the distal cap 240 are sealed by the outer surface of the tooltip 230. When the one or more openings 245 of the distal cap 240 are sealed by the outer surface of the tooltip 230, fluid communication is closed between the tooltip lumen 231 and the environment.

In the extended position P2, the distal cap 240 at least partially opens fluid communication between the tooltip lumen 231 and the environment. In the extended position P2, the distal cap 240 extends distally past the tool tip 230 such that the one or more openings 245 of the distal cap 240 are not sealed by the outer surface of the tooltip 230. When the one or more openings 245 of the distal cap 240 are not sealed by the outer surface of the tooltip 230, fluid communication is open between the tooltip lumen 231 and the environment.

In other words, the distal cap 240 may selectively open and close fluid communication between the environment and the tooltip lumen 231. The distal cap 240 may be selectively activated to open fluid communication between the tooltip lumen 231 and the environment, for example, to deliver a fluid (e.g., contrast dye) into a patient's bloodstream.

In another embodiment shown in FIGS. 4A-4D, the distal cap 340 may selectively open and close fluid communication between the environment and an electrode disposed on the tooltip 330. In such embodiments, the distal cap 340 may selectively open fluid communication between the environment and the electrode, for example, for pacing or for delivery of energy (e.g., electrical energy, such as for pacing or defibrillation). In such an embodiment, the electrode disposed on the tooltip may be a passive electrode. The electrode disposed on the tooltip may be accompanied by or coupled to a second electrode (e.g., a ring electrode 232 shown in FIGS. 3A-3C or a ring electrode 335 shown in FIGS. 4A-4D). Additionally or alternatively, delivery of energy may be used for sensing or mapping the environment, for example, before delivering or fixing an implant, such as an implantable electrode.

According to an embodiment, the medical device 300 includes a tubular body 310 defining a longitudinal axis A310. The tubular body 310 has at least one inner lumen 312. The inner lumen 312 may extend parallel to or along the longitudinal axis A310. The inner lumen 312 may extend along part of the length of the tubular body 310 or along the entire length of the tubular body 310. The medical device 300 includes an inflatable balloon 320, a tooltip 330, and a balloon-actuated distal cap 340.

The medical device 300 includes a tooltip 330 attached to the tubular body 310 at the distal end 313 of the tubular body 310. The tooltip 330 may include a plurality of tools that may be selectively exposed by actuating the cap 340 using the inflatable balloon 320. In the embodiment shown, the tooltip 330 includes three electrodes 331, 332, 333 disposed at different axial distances about the tooltip circumference. Between each of the three electrodes 331, 332, 333 are O-ring seals 334. Another O-ring seal 334 may be disposed proximally of the proximal-most electrode 331. Another O-ring seal 334 may be disposed distally of the distal-most electrode 333. The O-ring seals 334 may be sized to seal against the inside surface of the cap 340. According to an embodiment, the cap 340 includes an opening 345 through the side wall of the cap 340. When the cap 340 is axially translated by the balloon 320, the opening 345 may be selectively aligned with one of the electrodes 331, 332, 333, opening fluid communication between the electrode 331, 332, or 333 and the environment.

Figure 4A:
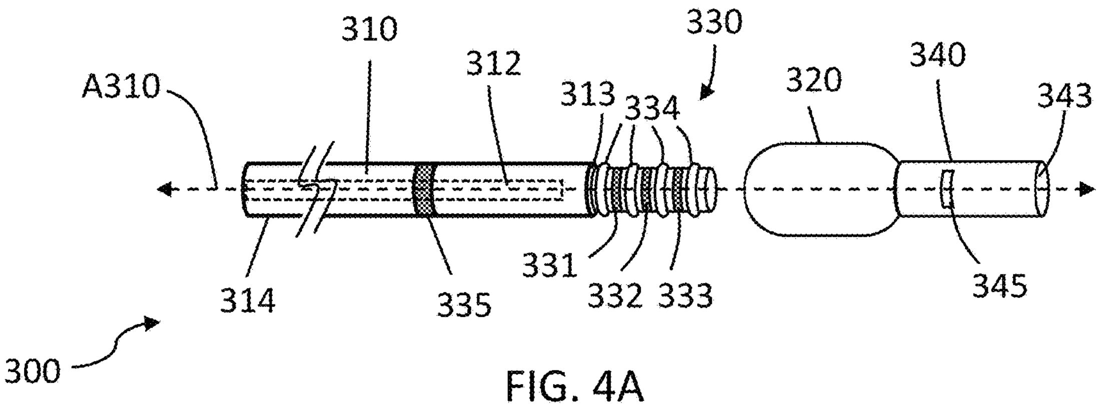
FIG. 4A is a partially exploded perspective view of a medical device in accordance with one or more embodiments of the present disclosure.
Figure 4B:
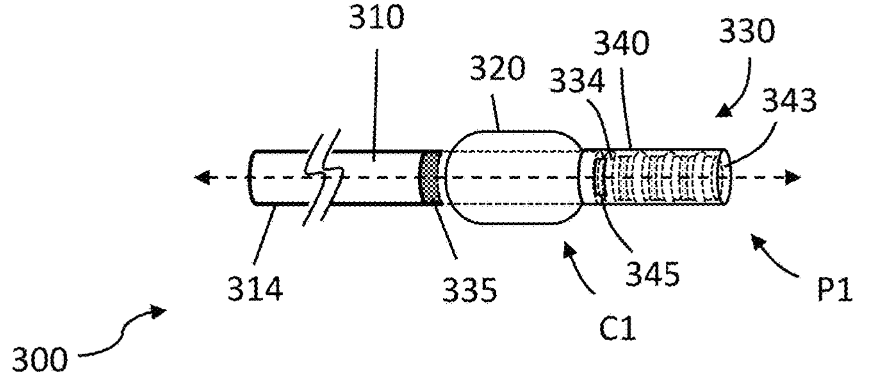
FIG. 4B is a perspective view of the medical device of FIG. 4A with a distal cap in a retracted position.
Figure 4C:
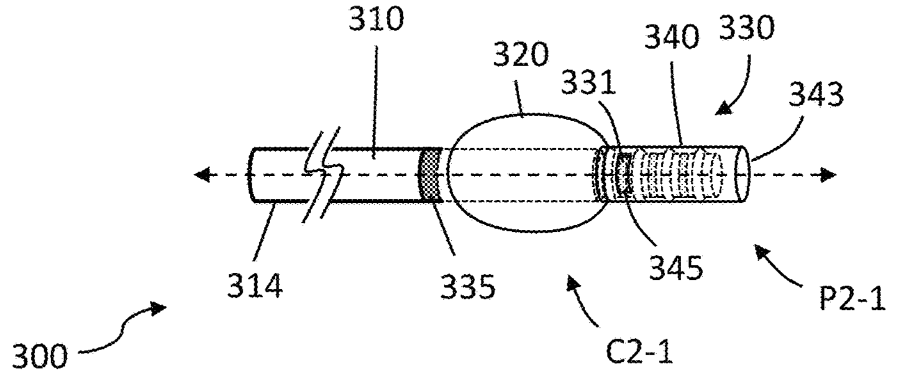
FIG. 4C is a perspective view of the medical device of FIG. 4A with the distal cap in a first extended position.
Figure 4D:
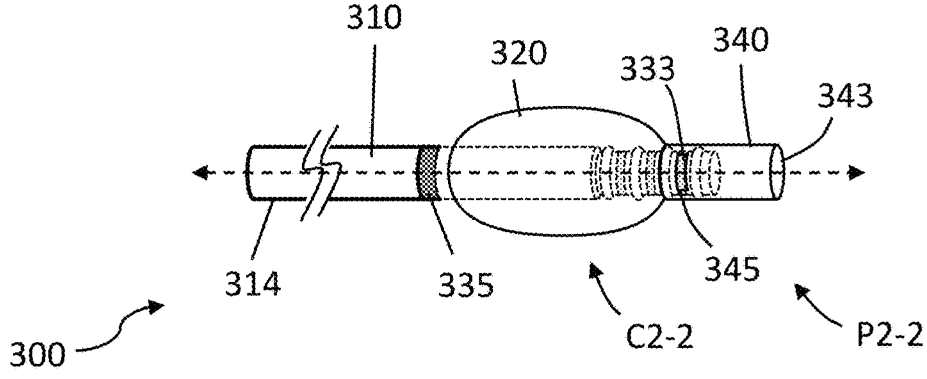
FIG. 4D is a perspective view of the medical device of FIG. 4A with the distal cap in a second extended position.

According to an embodiment, the distal cap 340 is translatably coupled to the balloon 320. The distal cap 340 is translatable along the longitudinal axis A310 between a retracted position P1 (FIG. 4B) and one or more extended positions P2-1, P2-2 (FIGS. 4C and 4D). The distal cap 340 telescopically receives the tooltip 330.

The balloon 320 has a deflated configuration C1 and one or more inflated configurations C2-1, C2-2. According to an embodiment, when the balloon 320 is in the deflated configuration C1, the distal cap 340 is in the retracted position P1. In the retracted position P1, the window 345 is positioned proximally of the proximal-most O-ring seal 334. Because the cap 340 has a closed end 343, none of the electrodes 331, 332, 333 are in fluid communication with the environment. When the balloon 320 is in the first inflated configuration C2-1, the distal cap 340 is in the first extended position P2-1. In the first extended position P2-1, the window 345 is aligned with the proximal-most electrode 331 and the proximal-most electrode 331 is in fluid communication with the environment. The first inflated configuration C2-1 may be a partially inflated configuration and the first extended position P2-1 may be a partially extended position. When the balloon 320 is in the second inflated configuration C2-2, the distal cap 340 is in the second extended position P2-2. In the second extended position P2-2, the window 345 is aligned with the distal-most electrode 333 and the distal-most electrode 333 is in fluid communication with the environment. The second inflated configuration C2-2 may be a fully inflated configuration and the second extended position P2-2 may be a fully extended position. The balloon 320 and cap 340 may have additional partially extended configurations and positions, not shown.

In other words, the distal cap 340 may selectively open and close fluid communication between the environment and one of a plurality of tools, such as the electrodes 331, 332, 333. The distal cap 340 may be selectively activated to open fluid communication between the tooltip 330 and the environment, for example, to deliver energy (e.g., electrical energy, such as for pacing or defibrillation). The delivery of energy may be used for sensing or mapping the environment.

In one or more embodiments, the balloon-actuatable sheath of the present disclosure may be used as part of a medical device, such as an implantable medical device. For example, an embodiment of the medical device 400, as shown in a patient 10 in FIG. 5, may be provided that may be used to deliver pacing leads to the patient's heart 30. In such an embodiment, the pacing leads may be incorporated into the medical device 400 and extend from the proximal end of the tubular body 410 to connect to the implantable medical device 20. Electrodes may be located at the distal end of the tubular body 410 and electrically connectable to the tool, such as a screw-in helix for active fixation of the leads.

Figure 5:
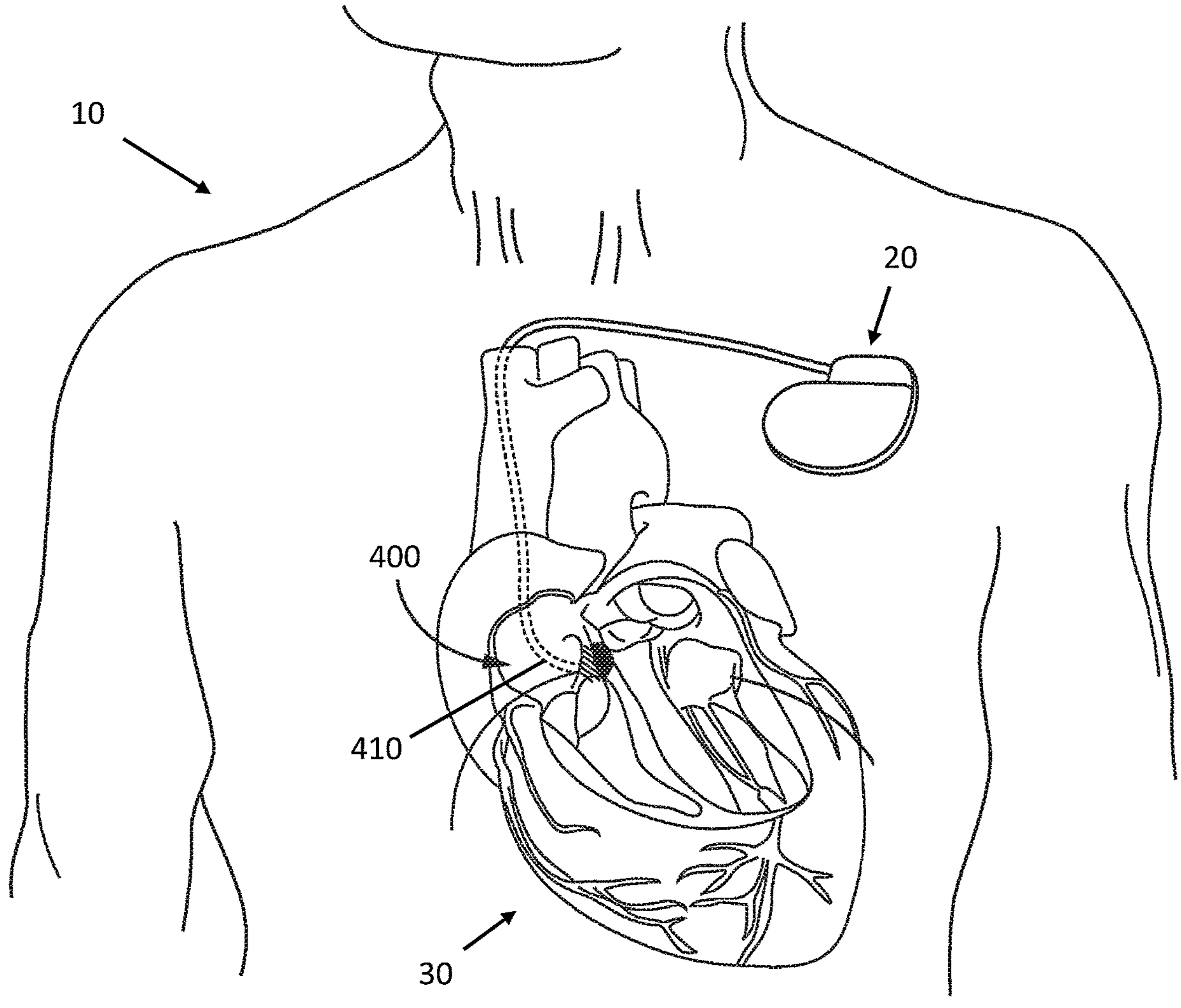
FIG. 5 is a schematic depiction of a medical device in accordance with one or more embodiments of the present disclosure, in use in a patient's body.

While FIG. 5 shows the medical device 400 connected to an implantable medical device 20, embodiments of the medical device may be connected to other types of medical devices, such as external medical devices or wearable medical devices.

Pacing leads, such as according to the embodiment shown in FIG. 5 may be fixated to the heart temporarily (that is configured to be removed after a short and/or definite length of time, such as during a surgical procedure, during an out-patient hospital stay, during an in-patient hospital stay, after 1 hour, after 12 hours, after 24 hours, after 1 week, after 1 month, or after 6 months), semi-permanently (that is, configured to be removed from the patient after a long or indefinite length of time, such as after 1 month, after 6 months, after 12 months, or after 5 years), or permanently (that is, configured not to be removed from the patient). Likewise, other embodiments may be configured for temporary, semi-permanent, or permanent use inside the patient's body.

According to an embodiment, a method of using the medical device of the present disclosure includes inserting the distal end of the tubular body through an introduction site of the patient, then at least partially inflating the balloon to extend a tubular sheath translatably attached to the balloon. The balloon extends circumferentially around and is fixedly attached to the tubular body. The tubular sheath is extended to at least partially surround the tooltip located at the distal end of the tubular body. The method proceeds by advancing the medical device through the patient's body from the insertion site to the target site, and then at least partially deflating the balloon to retract the tubular sheath.

The tool tip may then be used at the target site, for example, to fixate pacing leads to the patient's heart or to administer a pharmaceutical.

According to an embodiment, a method of using the medical device of the present disclosure includes inserting the distal end of the tubular body of the medical device through an introduction site of a patient; at least partially inflating the balloon; advancing the medical device through the patient from the introduction site to a target site; and using the tooltip at the target site. In some embodiments, the balloon is at least partially inflated prior to advancing the medical device through the patient from the introduction site to a target site and deflated after advancing and prior to using the tooltip at the target site. In other embodiments, the balloon is at least partially inflated after advancing the medical device through the patient from the introduction site to a target site and prior to using the tooltip at the target site.

EXEMPLARY EMBODIMENTS

The following is a list of exemplary embodiments according to the present disclosure.

Embodiment 1 is a medical device comprising:

- a tubular body defining a longitudinal axis, the tubular body comprising: a distal end; an inner lumen extending along the longitudinal axis; and an outer surface;
- a tooltip attached to the tubular body at the distal end of the tubular body;
- a balloon extending circumferentially around the tubular body, the balloon comprising: a proximal portion fixedly coupled to the tubular body; a distal portion; and a radially inflatable middle portion between the proximal portion and the distal portion of the balloon, the inflatable middle portion comprising an inner volume in fluid communication with the inner lumen of the tubular body; and
- a tubular sheath comprising a distal opening, translatably coupled to the balloon at the distal portion of the balloon, the tubular sheath being translatable along the longitudinal axis between a retracted position and an extended position, wherein in the extended position, the tubular sheath at least partially surrounds the tooltip.

Embodiment 2 is a medical device comprising: a tubular body defining a longitudinal axis, the tubular body comprising: a distal end; an inner lumen extending along the longitudinal axis; and an outer surface;

- a tooltip attached to the tubular body at the distal end of the tubular body;
- a balloon extending circumferentially around the tubular body, the balloon comprising: a proximal portion fixedly coupled to the tubular body; a distal portion; and a radially inflatable middle portion between the proximal portion and the distal portion of the balloon, the inflatable middle portion comprising an inner volume in fluid communication with the inner lumen of the tubular body; and
- a distal cap comprising one or more openings, translatably coupled to the balloon at the distal portion of the balloon, the distal cap being translatable along the longitudinal axis between a retracted position and an extended position, wherein in the extended position, the distal cap at least partially opens fluid communication between the tooltip and an environment.

Embodiment 3 is the medical device of embodiment 2, wherein the tooltip comprises a tooltip lumen extending along the longitudinal axis and wherein in the extended position, the distal cap at least partially opens fluid communication between the tooltip lumen and an environment.

Embodiment 4 is the medical device of embodiment 2, wherein the tooltip comprises an electrode and wherein in the extended position, the distal cap opens fluid communication between the electrode and an environment.

Embodiment 5 is the medical device of embodiment 4, wherein the tooltip comprises a plurality of electrodes and wherein the distal cap has a first extended position that opens fluid communication between a first electrode and the environment and a second extended position that opens fluid communication between a second electrode and the environment.

Embodiment 6 is the medical device of any one of the preceding embodiments, wherein the balloon has an inflated configuration, wherein when the balloon is in the inflated configuration, the tubular sheath or the distal cap is in the extended position.

Embodiment 7 is the medical device of any one of the preceding embodiments, wherein the balloon has a deflated configuration, wherein when the balloon is in the deflated configuration, the tubular sheath or the distal cap is in the retracted position.

Embodiment 8 is the medical device of any one of the preceding embodiments, wherein when the balloon is in the deflated configuration, the balloon has a wall thickness between 0.1 mm and 1 mm. The wall thickness of the balloon in the deflated configuration may be 0.1 mm or greater, 0.125 mm or greater, 0.15 mm or greater, 0.2 mm or greater, or 0.3 mm or greater. The wall thickness of the balloon in the deflated configuration may be 1 mm or less, 0.75 mm or less, 0.5 mm or less, 0.4 mm or less, or 0.3 mm or less.

Embodiment 9 is the medical device of any one of the preceding embodiments, wherein when the balloon is in the deflated configuration, the balloon has an internal diameter of between 0.5 mm or greater, 0.75 mm or greater, 1 mm or greater, 1.5 mm or greater, or 2 mm or greater. The internal diameter of the balloon in the deflated configuration may be 4 mm or less, 3 mm or less, or 2 mm or less.

Embodiment 10 is the medical device of any one of the preceding embodiments, wherein the tubular body further comprises a proximal end in fluid communication with an attachment coupling.

Embodiment 11 is the medical device of embodiment 6, wherein the proximal portion of the balloon is attached to the tubular body between the proximal end and the distal end of the tubular body.

Embodiment 12 is the medical device of any one of the preceding embodiments, wherein the tooltip comprises a fixation mechanism.

Embodiment 13 is the medical device of embodiment 8, wherein the tooltip comprises an active fixation mechanism.

Embodiment 14 is the medical device of any one of the preceding embodiments, wherein the tooltip comprises a helix, a blade, a lead, or an electrode.

Embodiment 15 is the medical device of any one of the preceding embodiments, wherein the tooltip comprises a hypodermic needle fluidly couplable to the at least one inner lumen of the tubular body.

Embodiment 16 is the medical device of any one of the preceding embodiments, wherein the tooltip comprises an anti-inflammatory steroid or an anticoagulant.

Embodiment 17 is the medical device of any one of the preceding embodiments, wherein the tooltip is releasably attached at the distal end of the tubular body.

Embodiment 18 is the medical device of any one of the preceding embodiments, wherein the tubular sheath or the distal cap further comprises a second tooltip.

Embodiment 19 is the medical device of any one of the preceding embodiments, wherein the balloon comprises silicone.

Embodiment 20 is the medical device of any one of the preceding embodiments, wherein the distal portion of the balloon is fixedly coupled to the tubular body.

Embodiment 21 is the medical device of any one of the preceding embodiments, wherein the balloon comprises latex.

Embodiment 22 is the medical device of any one of the preceding embodiments, wherein the balloon comprises an elastomer.

Embodiment 23 is the medical device of any one of the preceding embodiments, wherein the tubular sheath or the distal cap is substantially conical.

Embodiment 24 is the medical device of any one of the preceding embodiments, wherein the tubular sheath or the distal cap is substantially cylindrical.

Embodiment 25 is the medical device of any one of the preceding embodiments, wherein the tubular sheath or the distal cap comprises plastic, glass, or metal.

Embodiment 26 is the medical device of any one of the preceding embodiments, wherein the tubular sheath or the distal cap comprises silicon, latex, polyurethane, polytetrafluoroethylene, or polyetheretherketone.

Embodiment 27 is the medical device of any one of the preceding embodiments, wherein the tubular sheath or the distal cap comprises platinum, iridium, titanium, stainless steel, or nitinol.

Embodiment 28 is the medical device of any one of the preceding embodiments, wherein the tubular body comprises plastic, glass, or metal.

Embodiment 29 is the medical device of any one of the preceding embodiments, wherein the tubular body comprises a thermoplastic.

Embodiment 30 is the medical device of any one of the preceding embodiments, wherein the tubular body comprises polyurethane, CARBOTHANE™, PELLETHANE®, ELASTHANE™ polyether block amide, ARNITEL®, or silicone.

Embodiment 31 is the medical device of any one of the preceding embodiments, wherein the tubular body comprises braided metal.

Embodiment 32 is the medical device of any one of the preceding embodiments, wherein the tubular body comprises a metal coil.

Embodiment 33 is the medical device of any one of the preceding embodiments, wherein the tubular body has an outer diameter between 0.5 mm and 4 mm, the outer diameter of the tubular body may be 0.5 mm or greater, 0.75 mm or greater, 1 mm or greater, 1.5 mm or greater, or 2 mm or greater, the outer diameter of the tubular body may be 4 mm or less, 3 mm or less, or 2 mm or less.

Embodiment 34 is the medical device of any one of the preceding embodiments, wherein the tubular body has a length of between 35 cm and 110 cm, the tubular body 110 may have an axial length of 35 cm or greater, 50 cm or greater, or 75 cm or greater, the tubular body 110 may have an axial length of 110 cm or less, 90 cm or less, or 80 cm or less.

Embodiment 35 is the medical device of any one of the preceding embodiments, wherein the outer surface of the tubular body comprises a circumferential channel, the proximal portion of the balloon being fixedly coupled at the circumferential channel of the tubular body.

Embodiment 36 is a method of using the medical device of any one of embodiments 1 to 35, the method comprising: inserting the distal end of the tubular body of the medical device through an introduction site of a patient; at least partially inflating the balloon; advancing the medical device through the patient from the introduction site to a target site; and using the tooltip at the target site.

Embodiment 37 is the method of embodiment 36, wherein the balloon is at least partially inflated prior to advancing the medical device through the patient from the introduction site to a target site and wherein the balloon is deflated after advancing and prior to using the tooltip at the target site.

Embodiment 38 is the method of embodiment 36, wherein the balloon is at least partially inflated after advancing the medical device through the patient from the introduction site to a target site and prior to using the tooltip at the target site.

Embodiment 39 is a method of using a medical device, the method comprising: inserting a distal end of a tubular body of the medical device through an introduction site of a patient; at least partially inflating a balloon extending circumferentially around and fixedly attached to the tubular body to extend a tubular sheath translatably attached to the balloon, wherein the tubular sheath is extended to at least partially surround a tooltip located at the distal end of the tubular body; advancing the medical device through the patient from the introduction site to a target site; at least partially deflating the balloon to retract the tubular sheath; and using the tooltip at the target site.

Embodiment 40 is the method of embodiment 39, wherein the balloon comprises a proximal portion fixedly coupled to the tubular body; a distal portion; and a radially inflatable middle portion between the proximal portion and the distal portion of the balloon, the inflatable middle portion comprising an inner volume in fluid communication with the inner lumen of the tubular body; and wherein the tubular sheath comprises a distal opening and is translatably coupled to the balloon at the distal portion of the balloon, the tubular sheath being translatable along the longitudinal axis between a retracted position and an extended position, wherein in the extended position, the tubular sheath at least partially surrounds the tooltip.

Embodiment 41 is the method of any one of embodiments 36 to 40, wherein the balloon has an inflated configuration, wherein when the balloon is in the inflated configuration, the tubular sheath is in the extended position.

Embodiment 42 is the method of any one of embodiments 36 to 41, wherein the balloon has a deflated configuration, wherein when the balloon is in the deflated configuration, the tubular sheath is in the retracted position.

Embodiment 43 is the method of any one of embodiments 36 to 42, wherein when the balloon is in the deflated configuration, the balloon has a wall thickness between 0.1 mm and 1 mm. The wall thickness of the balloon in the deflated configuration may be 0.1 mm or greater, 0.125 mm or greater, 0.15 mm or greater, 0.2 mm or greater, or 0.3 mm or greater. The wall thickness of the balloon in the deflated configuration may be 1 mm or less, 0.75 mm or less, 0.5 mm or less, 0.4 mm or less, or 0.3 mm or less.

Embodiment 44 is the method of any one of embodiments 36 to 43, wherein when the balloon is in the deflated configuration, the balloon has an internal diameter of between 0.5 mm or greater, 0.75 mm or greater, 1 mm or greater, 1.5 mm or greater, or 2 mm or greater. The internal diameter of the balloon in the deflated configuration may be 4 mm or less, 3 mm or less, or 2 mm or less.

Embodiment 45 is the method of any one of embodiments 36 to 44, wherein the tubular body further comprises a proximal end in fluid communication with an attachment coupling.

Embodiment 46 is the method of embodiment 45, wherein the proximal portion of the balloon is attached to the tubular body between the proximal end and the distal end of the tubular body.

Embodiment 47 is the method of any one of embodiments 36 to 46, wherein the tooltip comprises a fixation mechanism.

Embodiment 48 is the method of embodiment 47, wherein the tooltip comprises an active fixation mechanism.

Embodiment 49 is the method of any one of embodiments 36 to 48, wherein the tooltip comprises a helix, a blade, a lead, or an electrode.

Embodiment 50 is the method of any one of embodiments 36 to 49, wherein the tooltip comprises a hypodermic needle fluidly couplable to the at least one inner lumen of the tubular body.

Embodiment 51 is the method of any one of embodiments 36 to 50, wherein the tooltip comprises an anti-inflammatory steroid or an anticoagulant.

Embodiment 52 is the method of any one of embodiments 36 to 51, wherein the tooltip is releasably attached at the distal end of the tubular body.

Embodiment 53 is the method of any one of embodiments 36 to 52, wherein the tubular sheath further comprises a second tooltip.

Embodiment 54 is the method of any one of embodiments 36 to 53, wherein the balloon comprises silicone.

Embodiment 55 is the method of any one of embodiments 36 to 54, wherein the distal portion of the balloon is fixedly coupled to the tubular body.

Embodiment 56 is the method of any one of embodiments 36 to 55, wherein the balloon comprises latex.

Embodiment 57 is the method of any one of embodiments 36 to 56, wherein the balloon comprises an elastomer.

Embodiment 58 is the method of any one of embodiments 36 to 57, wherein the tubular sheath is substantially conical.

Embodiment 59 is the method of any one of embodiments 36 to 58, wherein the tubular sheath is substantially cylindrical.

Embodiment 60 is the method of any one of embodiments 36 to 59, wherein the tubular sheath comprises plastic, glass, or metal.

Embodiment 61 is the method of any one of embodiments 36 to 60, wherein the tubular sheath comprises silicon, latex, polyurethane, polytetrafluoroethylene, or polyetheretherketone.

Embodiment 62 is the method of any one of embodiments 36 to 61, wherein the tubular sheath comprises platinum, iridium, titanium, stainless steel, or nitinol.

Embodiment 63 is the method of any one of embodiments 36 to 62, wherein the tubular body comprises plastic, glass, or metal.

Embodiment 64 is the method of any one of embodiments 36 to 63, wherein the tubular body comprises a thermoplastic.

Embodiment 65 is the method of any one of embodiments 36 to 64, wherein the tubular body comprises polyurethane, CARBOTHANE™, PELLETHANE®, ELASTHANE™, polyether block amide, ARNITEL®, or silicone.

Embodiment 66 is the method of any one of embodiments 36 to 65, wherein the tubular body comprises braided metal.

Embodiment 67 is the method of any one of embodiments 36 to 66, wherein the tubular body comprises a metal coil.

Embodiment 68 is the method of any one of embodiments 36 to 67, wherein the tubular body has an outer diameter between 0.5 mm and 4 mm, the outer diameter of the tubular body may be 0.5 mm or greater, 0.75 mm or greater, 1 mm or greater, 1.5 mm or greater, or 2 mm or greater, the outer diameter of the tubular body may be 4 mm or less, 3 mm or less, or 2 mm or less.

Embodiment 69 is the method of any one of embodiments 36 to 68, wherein the tubular body has a length of between 35 cm and 110 cm, the tubular body 110 may have an axial length of 35 cm or greater, 50 cm or greater, or 75 cm or greater, the tubular body 110 may have an axial length of 110 cm or less, 90 cm or less, or 80 cm or less.

Embodiment 70 is the method of any one of embodiments 36 to 69, wherein the outer surface of the tubular body comprises a circumferential channel, the proximal portion of the balloon being fixedly coupled at the circumferential channel of the tubular body.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. It should be understood that this disclosure is not intended to be unduly limited by the illustrative embodiments and examples set forth herein and that such examples and embodiments are presented by way of example only with the scope of the disclosure intended to be limited only by the claims set forth here.

What is claimed:

1. A medical device comprising:

a tubular body defining a longitudinal axis, the tubular body comprising:
 a distal end;
 an inner lumen extending along the longitudinal axis; and
 an outer surface;
a tooltip attached to the tubular body at the distal end of the tubular body;
a balloon extending circumferentially around the tubular body, the balloon comprising:
 a proximal portion fixedly coupled to the tubular body;
 a distal portion; and
 a radially inflatable middle portion between the proximal portion and the distal portion of the balloon, the radially inflatable middle portion comprising an inner volume in fluid communication with the inner lumen of the tubular body; and
a tubular sheath comprising a distal opening, the tubular sheath being translatably coupled to the balloon at the distal portion of the balloon, the tubular sheath being translatable along the longitudinal axis between a retracted position and an extended position, wherein in the extended position, the tubular sheath at least partially surrounds the tooltip.

2. The medical device of claim 1, wherein the balloon has an inflated configuration, wherein when the balloon is in the inflated configuration, the tubular sheath is in the extended position.

3. The medical device of claim 2, wherein the balloon has a deflated configuration, wherein when the balloon is in the deflated configuration, the tubular sheath is in the retracted position.

4. The medical device of claim 3, wherein when the balloon is in the deflated configuration, the balloon has an internal diameter of between 0.5 mm and 4 mm.

5. The medical device of claim 1, wherein the tubular body further comprises a proximal end in fluid communication with an attachment coupling.

6. The medical device of claim 5, wherein the proximal portion of the balloon is attached to the tubular body between the proximal end and the distal end of the tubular body.

7. The medical device of claim 1, wherein the tooltip comprises a fixation mechanism.

8. The medical device of claim 7, wherein the fixation mechanism comprises an active fixation mechanism.

9. The medical device of claim 1, wherein the tooltip comprises a helix, a blade, a lead, or an electrode.

10. The medical device of claim 1, wherein the tooltip comprises a hypodermic needle fluidly couplable to the inner lumen of the tubular body.

11. The medical device of claim 1, wherein the tooltip comprises an anti-inflammatory steroid or an anticoagulant.

12. The medical device of claim 1, wherein the tubular sheath is substantially conical.

13. The medical device of claim 1, wherein the tubular sheath is substantially cylindrical.

14. The medical device of claim 1, wherein the tubular body has an outer diameter of between 0.5 mm and 4 mm.

15. The medical device of claim 1, wherein the outer surface of the tubular body comprises a circumferential channel, the proximal portion of the balloon being fixedly coupled at the circumferential channel of the tubular body.

* * * * *